(12) United States Patent
Howard

(10) Patent No.: US 8,398,573 B2
(45) Date of Patent: Mar. 19, 2013

(54) DRUJ BRACE WITH ULNAR STYLOID ACCOMMODATION

(75) Inventor: Wendy Marie Medeiros Howard, Haiku, HI (US)

(73) Assignee: Howard Therapy LLC, Keaau, HI (US)

( * ) Notice: Subject to any disclaimer, the term of this patent is extended or adjusted under 35 U.S.C. 154(b) by 71 days.

(21) Appl. No.: 11/857,434

(22) Filed: Sep. 18, 2007

(65) Prior Publication Data

US 2008/0071205 A1     Mar. 20, 2008

Related U.S. Application Data

(60) Provisional application No. 60/826,075, filed on Sep. 18, 2006.

(51) Int. Cl.
*A61F 5/00*     (2006.01)

(52) U.S. Cl. .................. 602/21; 602/5; 602/62; 602/64; 2/16

(58) Field of Classification Search .............. 602/5, 21, 602/62, 64, 75; 2/16, 162, 170
See application file for complete search history.

(56) References Cited

U.S. PATENT DOCUMENTS

| | | | | | |
|---|---|---|---|---|---|
| 923,217 | A | * | 6/1909 | Tyrrell | 602/64 |
| 949,716 | A | * | 2/1910 | Quenzer | 602/75 |
| 1,363,075 | A | * | 12/1920 | Adams | 602/60 |
| 4,040,632 | A | * | 8/1977 | Pawl | 473/213 |
| 4,176,839 | A | * | 12/1979 | Pinkus | 602/64 |
| 4,441,490 | A | * | 4/1984 | Nirschl | 602/21 |
| 5,160,314 | A | * | 11/1992 | Peters | 602/21 |
| 6,190,344 | B1 | * | 2/2001 | Bobroff | 602/21 |
| 6,383,157 | B1 | * | 5/2002 | Massi et al. | 602/21 |
| 6,691,351 | B1 | * | 2/2004 | Wharton | 5/628 |
| 7,037,286 | B1 | * | 5/2006 | Reinhardt | 602/21 |

OTHER PUBLICATIONS

PCT International Search Report, PCT/US2007/020366, mailing date Feb. 29, 2008, 6 pp.

* cited by examiner

*Primary Examiner* — Patricia Bianco
*Assistant Examiner* — Keri J Nelson
(74) *Attorney, Agent, or Firm* — Caesar, Rivise, Bernstein, Cohen & Pokotilow, Ltd.

(57) ABSTRACT

The DRUJ brace is donned circumferentially around the distal radioulnar joint and provides adjustable compression of the proximal portion of the distal radioulnar joint that is independent of adjustable compression of the distal portion of the distal radioulnar joint, without compression of the ulnar styloid. Compression is maintained by hook and loop fasteners.

10 Claims, 6 Drawing Sheets

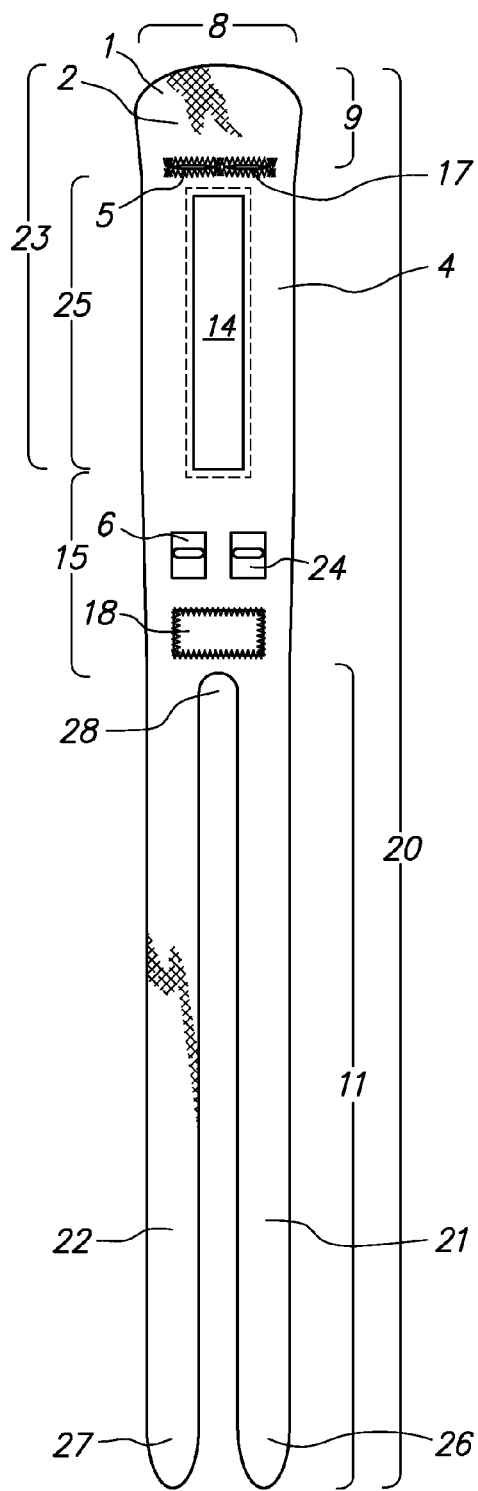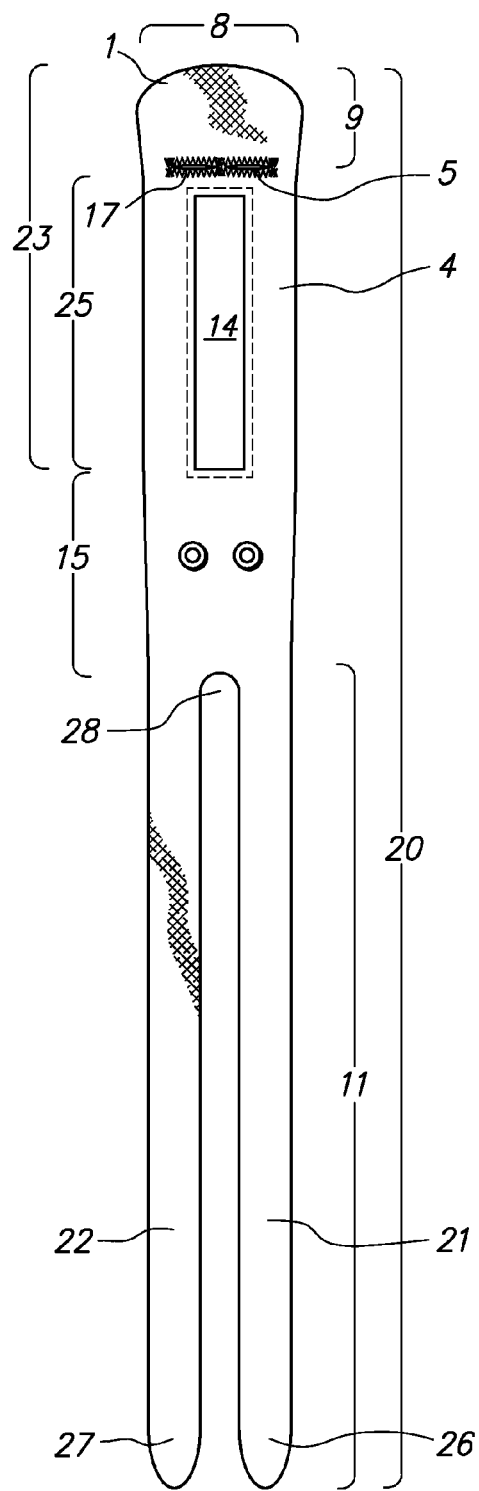

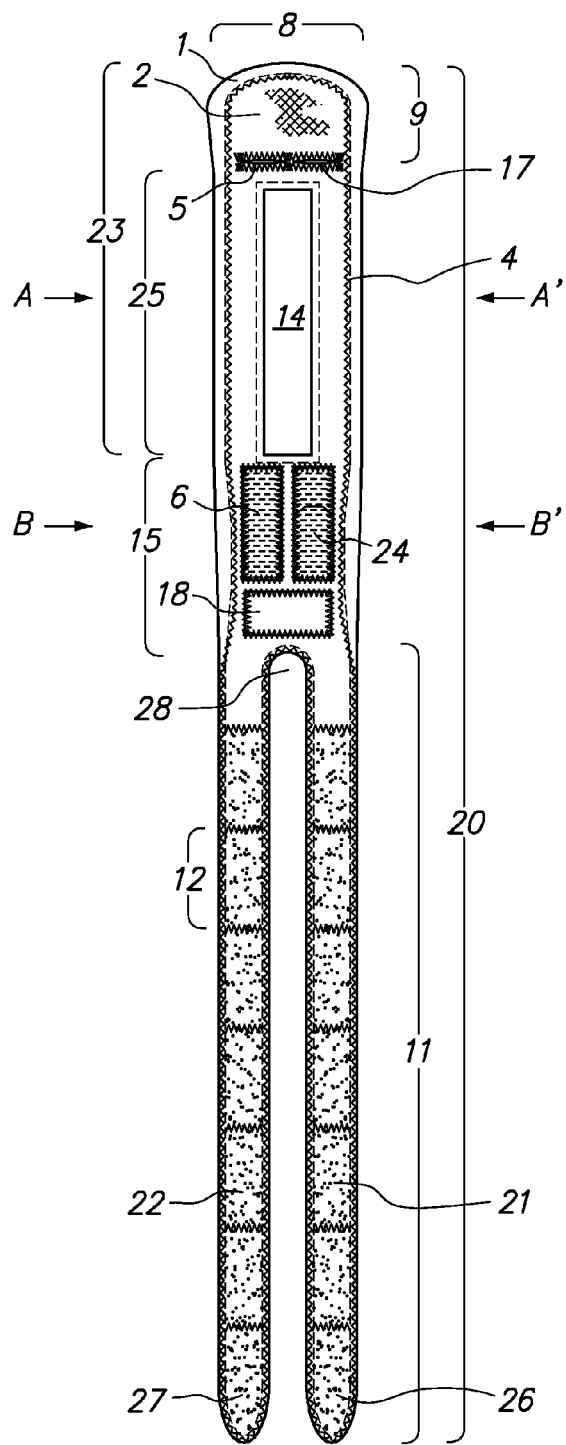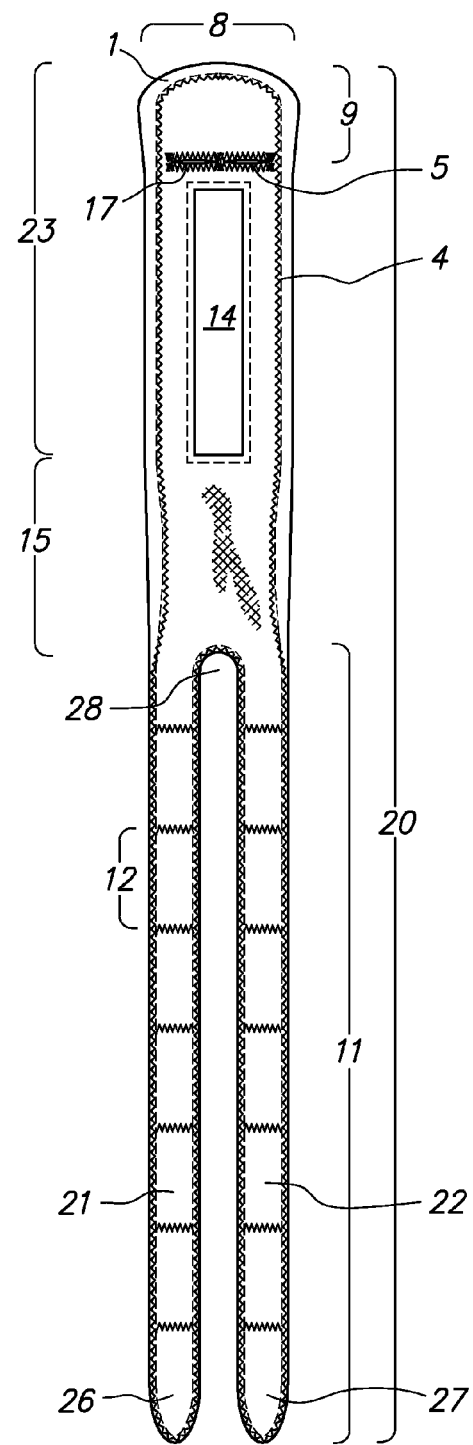

DRUJ BRACE WITH ULNAR STYLOID ACCOMMODATION

RELATED APPLICATION

This application claims the benefit of U.S. Provisional Patent Application No. 60/826,075, filed Sep. 19, 2006, the disclosures and drawings of which prior application are hereby incorporated by reference in their entirety.

BACKGROUND OF THE INVENTION

1. Field of Invention

This invention relates to orthopedic wrist braces, more particularly, to a novel brace affixed around the distal radioulnar joint ("DRUJ") that can be donned and doffed unilaterally, when worn does not compress or irritate the ulnar styloid and does not restrict wrist motion, and is significantly simpler, more effective, and less costly to manufacture than other types of wrist braces.

2. Description of the Related Art

A wide variety of wrist support devices are known in the art. The term "brace" as used herein means an orthopedic support device that does not contain a rigid or semi-rigid structural element. The term "splint" as used herein means an orthopedic support device that does contain a rigid or semi-rigid structural element to immobilize or partially immobilize a musculoskeletal region, typically a joint. The term "wrist" herein means the wrist of a person to which a wrist support device is affixed. The term "DRUJ area" means a band around the arm from the radiocarpal joint to a line approximately 15 mm proximal of the ulnar styloid. Severe pain can be associated with injury of the distal radioulnar joint.

A proximal row of bones in the wrist (i.e., scaphoid, lunate, triquetrum, and pisiform) articulate with the distal ends of the radius and ulna in a constrained space to allow three degrees of freedom at the wrist. Relative to the forearm, these hand movements include flexion-extension, pronation-supination, and radial/ulnar deviation. Relative stability of such mobility requires a coordinated system of ligaments, muscles, and tendons. The ulna represents the non-rotating, stable and weight-bearing part of the forearm around which the radius rotates in pronation and supination. The distal end of the radius together with the hand and what is held in the hand rest against the stable, immobile ulnar head, which acts as the keystone of the wrist. Mobility and stability of the distal radioulnar joint is accomplished by the combined action between fully congruent articulating surfaces and intact radioulnar ligaments. Following a distal radius fracture or other nearby trauma, the ulnar notch of the distal radius will frequently no longer be congruent to the ulnar head due to the displacement of the radius into dorsal angulation, radial angulation, or both angulations. In such an injury, stabilizing DRUJ ligaments often tear. Hagert, C. G, Handchir. Mikrochir. Plast. Chir. January 1994:26(1):22-26.

The triangular fibrocartilage complex ("TFCC") comprises the ligamentous and cartilaginous structures that suspend the distal radius and ulnar carpus from the distal ulna. The TFCC is the major ligamentous stabilizer of the DRUJ and the ulnar carpus. Humankind is differentiated from lower primates by a radiocarpal joint with a TFCC interposed between the ulna and carpus. The TFCC improves wrist functional stability and allows the above-mentioned three degrees of freedom at the wrist: flexion/extension, supination/pronation, and radial/ulnar deviation. Injuries to the DRUJ, especially to the TFCC, present with ulnar-sided wrist pain, frequently with "clicking" or "clunking".

The causes of wrist pain can be divided into three categories: mechanical, neurologic, and systemic. Psychosocial factors can also have a profound influence on wrist pain, particularly when the patient may be eligible for workers' compensation, so reduction of "wrist pain", which may in fact be localized to the DRUJ, is of great economic consequence. To prevent, or to ameliorate, post-traumatic, "wrist pain", a wrist brace or wrist splint is typically prescribed or adopted sua sponte, especially in connection with corrective osteotomy of the radius at a fracture site.

Correct compression of the distal radioulnar joint, or DRUJ, improves congruity between the ulnar notch of the radius and the head of the ulna, thereby providing prophylaxis for a subject at risk for DRUJ injury (or re-injury) and therapy for a subject during rehabilitation after surgery or a DRUJ or TFCC injury. Correct compression of the DRUJ reduces "wrist pain", especially for load-bearing tasks, when the injury is in the DRUJ or TFCC. Incorrect compression can exacerbate the injury.

User-applied orthopedic support devices are generally differentiated by (1) sleeve (aka pull-on), versus wrap, structure, (2) brace versus splint structure, (3) adjustability of the device, (4) limitations on joint motion when wearing the device, and (5) fastening means (e.g., D-ring, reclosable fasteners, straps and slits, lacing, clasps, snaps, buttons, hooks, rivets, and buckles). "Mating-halves" reclosable fasteners include hook and loop fasteners, e.g., Velcro® fasteners (Velcro Industries, Brampton, ON), and mushroom head fasteners, e.g., 3M® Dual Lock fasteners (3M, St. Paul, Minn.).

There are apparently no braces or splints designed specifically for the DRUJ. As of the application date, a search string of "distal radioulnar joint brace" and "distal radioulnar joint splint" returned no hits in major Internet search engines, and no U.S. patents or published applications contained in the title the term "distal radioulnar joint" and concern braces or splints. There are hundreds of designs for "wrist braces" and "wrist splints", but typically the structure of wrist braces and wrist splints covers at least the forearm, DRUJ, radiocarpal joint, metacarpals, and surround the base of the thumb; some braces and splints also cover the metacarpophalangeal joint and/or the elbow. The prophylactic and therapeutic objects of wrist braces and wrist splints are stabilization and immobilization, respectively, of the radiocarpal, metacarpal, and even metacarpophalangeal areas as distinct from the DRUJ, and DRUJ/TFCC. Currently available wrist braces and wrist splints (including specialized devices, such as ulnar deviation splints, wrist braces with metacarpophalangeal ("MCP") support, dorsal wrist cockups, wrist orthoses, pressure splints, wrist hinges, wrist wraps, and spica splints) can do more harm than good if only a DRUJ injury is involved, especially if full wrist motion is desired. In particular, "wrist wrap" type wrist braces, as a result of the elastic materials used in their construction, provide inadequate support for pronation and supination, and cannot be adjusted for load-bearing tasks. The ulnar styloid has no physical padding, is highly innervated, and is inherently vulnerable to bruising, irritation. and laceration. The deficiency of current wrist braces and wrist splints when used for DRUJ/TFCC support arises from undesirable abrasion and irritation of the ulnar styloid, compression of the radial and ulnar arteries, excessive compression of the proximal portion of the DRUJ (i.e., that part proximal to the ulnar styloid), inadequate compression of the distal portion of the DRUJ (i.e., that part distal to the ulnar styloid), complexity of fastening means preventing unilateral donning and doffing, and cost of manufacturing.

Patients who present with injuries to the TFCC describe severe pain and dysfunction to their wrists that surgeons are hesitant to treat surgically. Conservative treatment includes cortisone injections, and splinting of the elbow into 90 degrees of flexion and immobilizing the wrist in neutral. These treatments have substantially poor outcomes and dramatically high risk factors, including contractures of the elbow and wrist. In addition, these treatments are significantly disabling. When these patients present, they typically find that a circumferential squeezing of the DRUJ area can eliminate their "wrist pain" (in fact, they have DRUJ or DRUJ/TFCC pain). Many patients independently look for wrist wraps in the market place to recapture the effect of the pain-relieving squeeze. Wrist wraps, however, do not replicate the compressive force of the patient's opposite hand or a therapist's hands, especially in the area proximal to the radiocarpal joint.

The manufacturers of wrist braces and splints have arguably not properly characterized the problem of "wrist pain" by segmenting the problem into devices to treat pain distal to the radiocarpal joint and devices to treat pain proximal to the radiocarpal joint. The present invention expressly addresses the segment of "wrist pain" proximal to the radiocarpal joint (aka "ulnar-sided wrist pain"), i.e., pain associated with injury to the DRUJ or DRUJ/TFCC. The technical problem to be solved is to provide a DRUJ and TFCC support device that does not irritate or compress the ulnar styloid, provides adjustable compression of the proximal portion of the DRUJ that is independent of adjustable compression of the distal portion of the DRUJ, provides adequate support through pronation and supination, provides adjustment for load-bearing tasks, provides equal benefit on either the dextral or sinistral DRUJ area, and provides unilateral (using one hand) donning and doffing. It would be further desirable for the solution to this problem to avoid the use of fasteners that are difficult to use, that irritate the DRUJ area, and that add cost to manufacturing. It would be further desirable for the solution to this problem to be washable and durable, and to accommodate a range of DRUJ area circumferences, bilateral use, types of user activity (e.g., sports, office work, construction work), and price points.

SUMMARY OF THE INVENTION

The present invention, the DRUJ Brace with Ulnar Styloid Accommodation ("DRUJ Brace"), provides a DRUJ and TFCC support device that does not irritate or compress the ulnar styloid, does not compress the radial and ulnar arteries, provides adjustable compression of the proximal portion of the DRUJ that is independent of adjustable compression of the distal portion of the DRUJ, provides adequate support through pronation and supination, is adjustable for load-bearing tasks, is used with equal benefit on either the dextral or sinistral DRUJ area, and is doffed and donned unilaterally. The present invention uses a strap through slit compression means and the preferred embodiment avoids the use of D-rings, lacing, clasps, snaps, buttons, hooks, rivets, and buckles that are difficult to use, irritate DRUJ area, and add cost to manufacturing. The present invention is washable and durable and accommodates a range of DRUJ area circumferences, types of user activity, and price points.

A basic embodiment of the DRUJ Brace comprises a flexible, inelastic sheet ("primary sheet") adapted to wrap around the DRUJ area of a forearm of a human subject ("patient"). The primary sheet material is typically a washable, woven textile. The primary sheet comprises a central section, a first and a second strap connected to and disposed on one lateral side of the central section, a rounded end section longitudinally integral with (or connected to) the central section and opposite the two straps, a first slit in the end section aligned with the first strap, a second slit in the end section aligned with the second strap, a first fastening means in the central section aligned with the first strap, and a second fastening means in the central section aligned with the second strap. The area between the end section and the central section preferably has an oblong hole along the longitudinal axis of the DRUJ Brace, leaving two marginal areas of sheet material of approximately the same width as the two straps. The width of the end section is slightly greater than the width of the central section to allow the full width of each strap to pass through its corresponding slit in the end section. Each fastening means is preferably a mating-halves reclosable fastener with one mating-half on the top surface (i.e., centrifugal surface of the DRUJ Brace when the straps are engaged in the slits to create a cylindrical conformation of the DRUJ Brace) of the central section that mates with an opposite mating-half on the centripetal surface of a corresponding strap when the corresponding strap is engaged in its slit and folded back toward the central section.

A preferred embodiment has the structure of the preceding embodiment, but also has a second flexible, slightly elastic, sheet ("comfort sheet") underneath the entire area of the primary sheet and of the area between the end section and the central section (i.e., the comfort sheet covers the oblong, longitudinal hole in the primary sheet). The comfort sheet material is typically a washable, woven textile, with hemmed edges the wrap around the margins of the primary sheet. The comfort sheet preferably has a bottom surface with a soft, non-abrasive texture that contacts the patient's skin.

The DRUJ Brace can be donned three different ways with equal benefit. In one method of donning a DRUJ Brace with hook/loop fastening means, a patient guides the first strap through the corresponding first slit in the end section, guides the second strap through the corresponding second slit in the end section, thereby configuring the DRUJ Brace as a cylinder with two protruding straps, then slips the DRUJ Brace over the patient's hand and wrist until the central section of the DRUJ Brace overlies the dorsal surface of the DRUJ area with one strap skirting the distal side of the ulnar styloid ("distal strap") and the second strap skirting the proximal side of the ulnar styloid ("proximal strap"). The patient places the volar surface of the DRUJ Brace against a flat surface (e.g., a table, or the patient's flexed knee when sitting) to stabilize position of straps around the ulnar styloid, pulls both straps medially (i.e., back toward the central section) to tighten the DRUJ Brace around the DRUJ area, then firmly presses the centripetal mating portion of each strap against the corresponding mating portion of the fastening means on the top surface of the central section of the DRUJ Brace. The distal strap can be independently tensioned to apply an appropriate compressive force on the distal portion of the DRUJ. The proximal strap can be independently tensioned to apply an appropriate compressive force on the proximal portion of the DRUJ. The compressive force of each strap can be easily, rapidly, and independently adjusted by pulling a given strap off the fastening means on the central section, re-tensioning the strap, and firmly pressing the centripetal mating half of the reclosable fastener on the strap against the corresponding mating half on the central section of the DRUJ Brace. The excess length, if any, of the straps remains in dorsal DRUJ area, and does not invade the volar DRUJ area or interfere with typical patient activity, e.g., typing, bench work, personal hygiene, etc.

Once fitted with the DRUJ Brace, patients report decreased pain at rest, decreased pain with grip, decreased pain with supination, and increased function. In addition, use of the DRUJ Brace provides a substantial improvement in grip and weight bearing strength. If the patient presented with "clicking" and "clunking", such clicking and clunking is typically resolved with the use of the DRUJ Brace. The rehabilitative effects of use of the DRUJ Brace imply that spreading of the radius and ulna during supination exacerbates pathology of the TFCC. Use of the DRUJ Brace inhibits spreading of the radius and ulna during supination and allows for rest and healing of the TFCC. The DRUJ Brace is typically worn continuously for 6 weeks, has been enthusiastically adopted by patients, and is reported to be comfortable throughout such continuous use.

BRIEF DESCRIPTION OF THE DRAWINGS

FIG. 3 shows a top plan view of a basic embodiment of the DRUJ Brace constructed with a single textile sheet and equipped with fastening means comprising cam-lock fasteners affixed to the central section by rivets.

FIG. 4 shows a bottom plan view of a basic embodiment of the DRUJ Brace constructed with a single textile sheet and equipped with fastening means comprising riveted cam-lock fasteners.

FIG. 9. shows a top plan view of a two-sheet, textile embodiment of the DRUJ Brace equipped with fastening means comprising sewn-on, mating-halves reclosable fasteners.

FIG. 10. shows a bottom plan view of a two-sheet, textile embodiment of the DRUJ Brace equipped with fastening means comprising sewn-on, mating-halves reclosable fasteners.

DETAILED DESCRIPTION OF THE PREFERRED EMBODIMENTS

As used herein, "longitudinal" means parallel to the long axis of the forearm, and "lateral" means transverse to the longitudinal axis. With respect to a DRUJ Brace donned on the forearm of a subject, "longitudinal" means along the cylindrical axis of the DRUJ Brace, with the DRUJ Brace circumferentially enveloping the DRUJ area, and "lateral" means parallel to the DRUJ Brace straps as they circumferentially envelope the DRUJ area.

Figure 1:
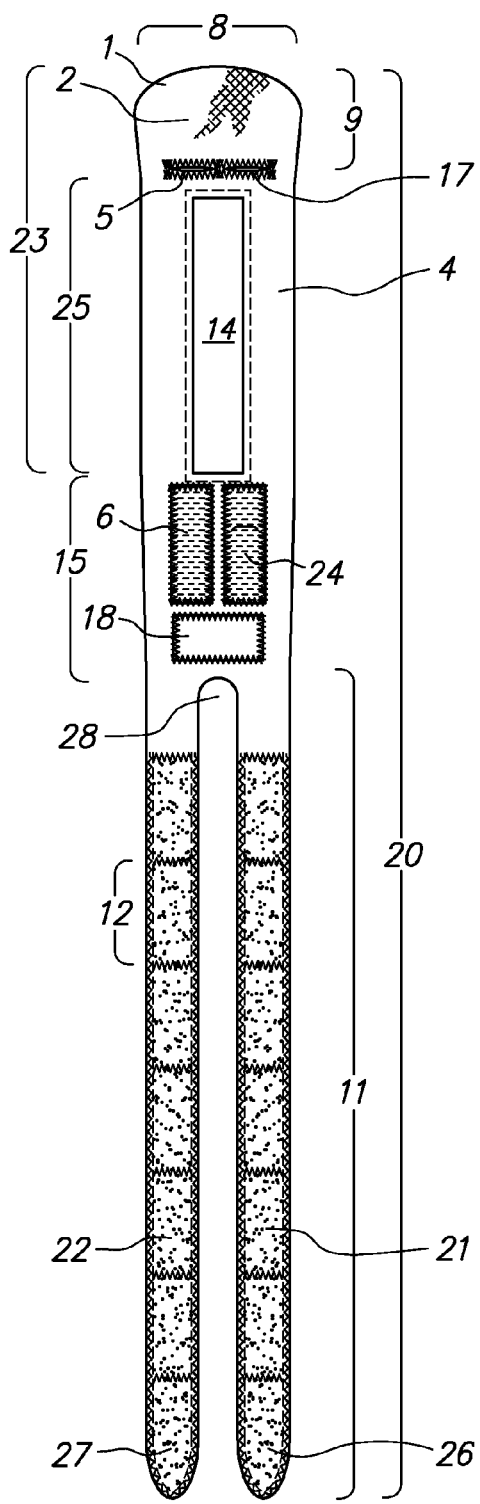
FIG. 1 shows a top plan view of a basic embodiment of the DRUJ Brace constructed with a single textile sheet and equipped with fastening means comprising mating-halves reclosable fasteners affixed to the central section by sewing.
Figure 2:
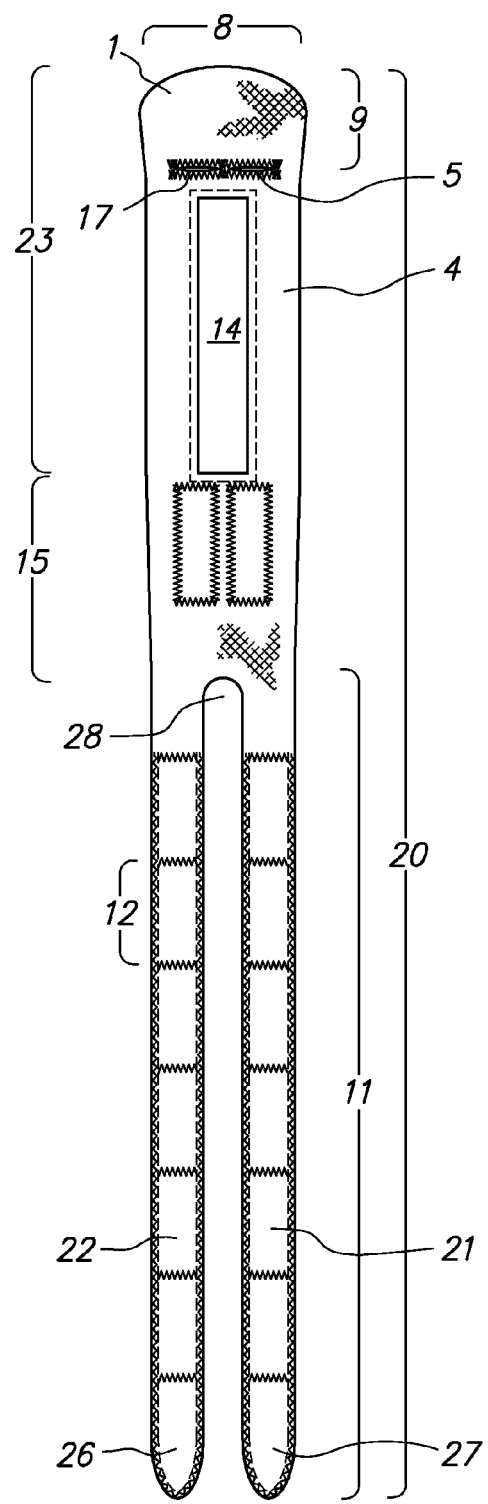
FIG. 2 shows a bottom plan view of a basic embodiment of the DRUJ Brace constructed with a single textile sheet and equipped with fastening means comprising sewn-on, mating-halves reclosable fasteners.

As shown in FIGS. 1 and 2, a basic embodiment of the DRUJ Brace (20) comprises a single flexible, inelastic sheet (1) adapted to wrap around the DRUJ area of a human subject ("patient"). The sheet (1) comprises a central section (15), a first strap (21) connected to, and disposed laterally on a "strap side" (11) of, the central section (15), a second strap (22) connected to, and disposed on the strap side (11) of, the central section (15) and parallel to first strap (21), a rounded end section (23) connected laterally to the central section (15) opposite the strap section (11), a first transverse slit (17) in the end section aligned with the first strap (21), a second transverse slit (5) in the end section (23) aligned with the second strap (22), a first fastening means half (24) in the central section aligned with the first strap (21), and a second fastening means half (6) in the central section aligned with the second strap (22). The width (8) of the terminal portion of the rounded grip section (9) is slightly greater than the width of the central section to allow slits (17, 5) wide enough for each respective strap (21, 22) to pass through its corresponding slit in the end section (23). The central section (15) is typically 4.5 to 7.0 cm in width.

A cutout section (25) is disposed between, and integrally attached to, a grip section (9) on one side and the central section (4) on the other side. The cutout section (25) contains a cutout (14) of the sheet (1) so that the remaining first marginal area and second marginal area are of approximately the same width as the first strap (21) and second strap (22), respectively. A label (18) can be affixed to the DRUJ Brace.

The "top" of a DRUJ Brace is the surface of the sheet (1) on which central fastening means halves (24, 6) are affixed. The "bottom" of a DRUJ Brace is the surface of the DRUJ Brace in immediate contact with the skin. Mating halves of the fasteners are attached to the straps (21, 22) of the sheet (1) on the same side of the sheet (1) as the central fastening means halves (24, 6). FIGS. 1, 5, 7, and 9 show by speckling the mating portions of hook and loop fasteners.

Figure 14:
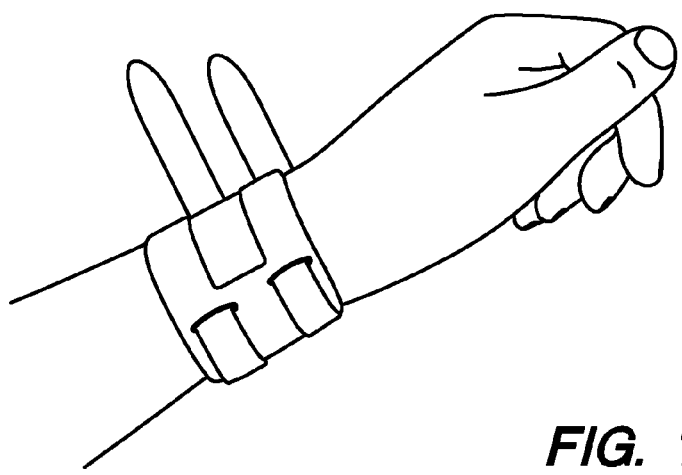
FIG. 14 shows a perspective view of a first way of wearing a DRUJ Brace.
Figure 15:
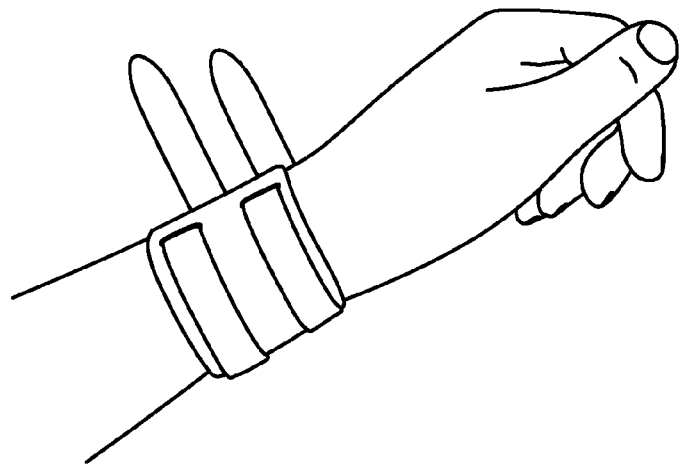
FIG. 15 shows a perspective view of a second way of wearing a DRUJ Brace.

To "don" a DRUJ Brace means the process of: (A) inserting the first strap (21) through its corresponding slit (17) and the second strap (22) through its corresponding slit (5) so that end section (23), including cutout section (25), central section (15), and straps (21, 22) folded back over the central section to form an approximately fist-sized cylinder with the mating portions of the fastening means on the central section and on the straps juxtaposed for engagement; (B) sliding a patient's hand and wrist through the cylinder of the DRUJ Brace and positioning the DRUJ Brace over the DRUJ area so that one strap, or marginal area of the cutout section, is proximal to the ulnar styloid, and the other strap, or other marginal area of the cutout section, is distal to the ulnar styloid; (C) tensioning the straps by pulling each strap further through its corresponding slit (a U is formed by each strap as it passes through its corresponding slit and back toward the central section); and (D) fastening each strap, still under tension, to the central section using the mating halves of the fastening means associated with each strap and the central section. As implied in step B, the DRUJ Brace can be positioned around the ulnar styloid in two different ways according to the preference of the patient donning the DRUJ Brace: in a first method of use, the cutout (14) surrounds the ulnar styloid; alternatively, the fastened straps (21, 22) run on either side of the ulnar styloid, as shown in FIGS. 14 and 15. The DRUJ Brace can be donned so that the terminal ends of the straps face medially or laterally. The orientation of the DRUJ Brace is selected to provide the maximum reduction of pain in the DRUJ area.

To "doff" a DRUJ Brace means the process of: (A) loosening each strap by separating the mating halves of each fastening means; (B) pulling on the grip section (9) of the end section (23) to expand the cylinder of the DRUJ Brace to a fist-sized circumference; and (C) withdrawing the patient's hand from the cylinder.

If "mating-halves" reclosable fasteners, such as hook and loop, or mushroom head, are used as the first and second fastening means, a mating half of each fastening means (24, 6) is affixed to the central section (15) and the opposite mating half of each fastening means is affixed to the first and second straps (21, 22) so that when a given strap is inserted through its corresponding slit in the end section (23) and pulled back toward the central section (15) to tension the strap, each mating half in the central section can engage the corresponding opposite mating half on each strap and while engaged maintain the strap tension. Mating-halves reclosable fasteners are preferred fastening means in view of their ease of fastening and adjustment.

In the "dispensing form" of a DRUJ Brace, the straps are not inserted through the corresponding slits; rather, the DRUJ Brace is planar and the dimension from the edge of the end section (23) to the tips of the straps (21, 22) is called the "planar width" (20) and the central axis in the dispensing form from the terminal edge of the end section (23) to the tips of the straps (21, 22) is called the "lateral axis". The planar length (8) is transverse to the planar width (8); the longitudinal axis is transverse to the lateral axis.

Adult wrist vary in circumference from 25 to 80 mm. An adult size DRUJ Brace has a planar width from 25 cm to 60 cm, of which planar width, the lateral dimension of (A) the lateral dimension (11) of each strap is approximately 50% of the planar width, (B) the central section width is approximately 15% of the planar width, (C) the cutout section width is approximately 25% of the planar width, and (D) the end section width is approximately 10% of the planar width. For example, for a DRUJ Brace with a planar width of 30 cm, the lateral dimension of each strap is approximately 15 cm, the central section (15) is approximately 4.5 cm, the cutout section is approximately 7.5 cm, and the grip section (9) is approximately 3 cm.

An adult size DRUJ Brace has a planar length that tapers from approximately 4.4 cm in the grip section (9) to approximately 3.4 cm in the strap tips (26, 27)). The planar length can vary from 30 to 60 mm to accommodate variation in patients. The planar length of each strap (21, 22) is approximately 1.3 cm, other than the area of the strap tips (26, 27) and of the crotch (28) where the straps join the central section (15). The gap between the straps is approximately 0.8 cm, other than the area of the strap tips (26, 27), where the strap gap increases toward the strap tips, and of the crotch (28), where the strap gap decreases as the straps join the central section (15). The planar length of the cutout (14) is approximately 1.2 cm. At the junction of the cutout (14) with the grip section (9), the planar length of the each marginal area (a marginal area is each of two sections of the sheet (1) that connect the grip section (9) to the central section (15) and thereby delimit the cutout (14)) is approximately 1.4 cm. At the junction of the cutout (14) with the central section (15), the planar length of the each marginal area is approximately 1.3 cm. The planar length of each slit (17, 5) is approximately 1.4 cm and otherwise sufficient to allow the passage of the corresponding strap and tensioning of each strap during donning of a DRUJ Brace. Dimensions of pediatric sizes of DRUJ Braces are proportionally smaller. A DRUJ Brace is approximately 2 mm thick.

The cutout (14), and the strap gap separating the first (21) and second (22) straps, and the placement of the cutout (14) or strap gap around the ulnar styloid, avoid irritation, contusion, or laceration in the area of the ulnar styloid. After the DRUJ Brace is donned, no pressure is applied to the ulnar styloid. The distal and proximal straps clear the wrist crease and allow full flexion and extension of the wrist without any irritation to the wrist. The cutout (14) is necessary to provide a way, described below, of donning a DRUJ Brace so that the cutout surrounds the ulnar styloid. It is also a way to accommodate flexibility of the brace with end range wrist extension and to enable independent adjustment of the compression exerted by each engaged (fastened) strap.

FIG. 1 shows a top plan view of a basic embodiment of the DRUJ Brace constructed with a single textile sheet (1) and equipped with fastening means comprising mating-halves reclosable fasteners, such as hook and loop or mushroom head, affixed to the top of the sheet in the central section and on each strap by sewing. Other means known in the art of attachment of mating-halves reclosable fasteners can be used, e.g., adhesives, heat welding, and heat fusion.

FIG. 2 shows a bottom plan view of a basic embodiment of the DRUJ Brace constructed with a single textile sheet (1) and equipped with fastening means comprising sewn-on mating-halves reclosable fasteners.

FIG. 3 shows a top plan view of a basic embodiment of the DRUJ Brace constructed with a single textile sheet and equipped with fastening means comprising cam-lock fasteners affixed to the central section by rivets. Other means known in the art of attachment of cam-lock fasteners can be used, e.g., adhesives, heat welding, and heat fusion.

FIG. 4 shows a bottom plan view of a basic embodiment of the DRUJ Brace constructed with a single textile sheet and equipped with fastening means comprising riveted cam-lock fasteners.

Figure 5:
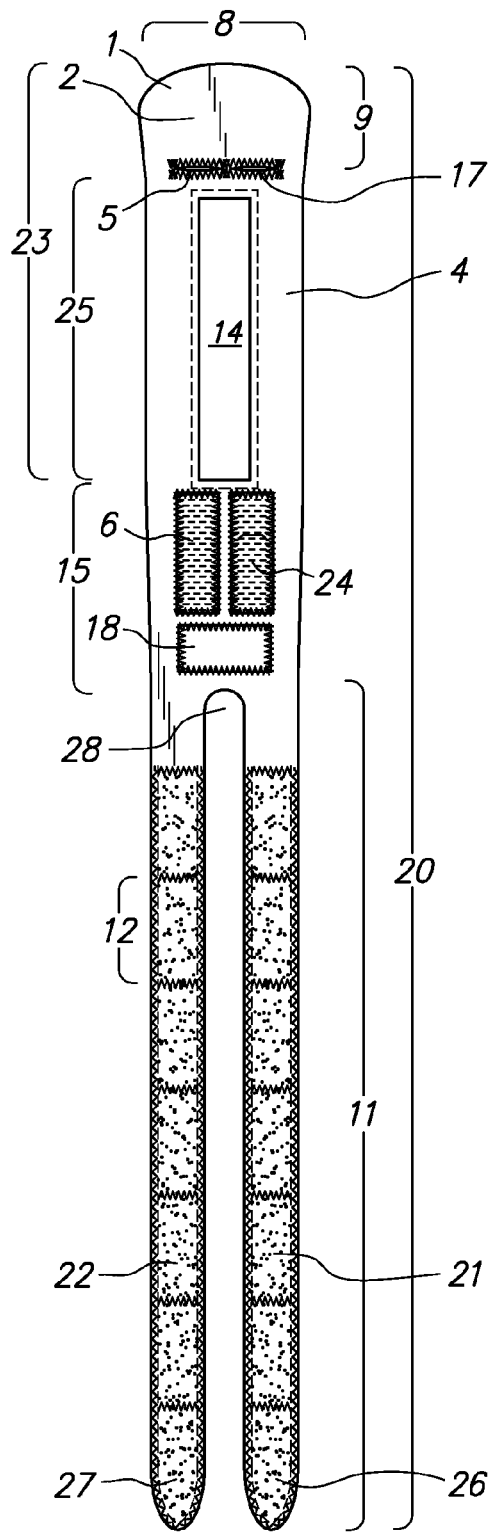
FIG. 5 shows a top plan view of a basic embodiment of the DRUJ Brace constructed with a single plastic sheet and equipped with fastening means comprising mating-halves reclosable fasteners affixed to the top of the sheet during injection molding.

FIG. 5 shows a top plan view of a basic embodiment of the DRUJ Brace constructed with a single plastic sheet and equipped with fastening means comprising mating-halves reclosable fasteners, such as hook and loop or mushroom head, affixed to the top of the sheet. The sheet can be injection molded, and fastening means affixed during injection molding.

Figure 6:
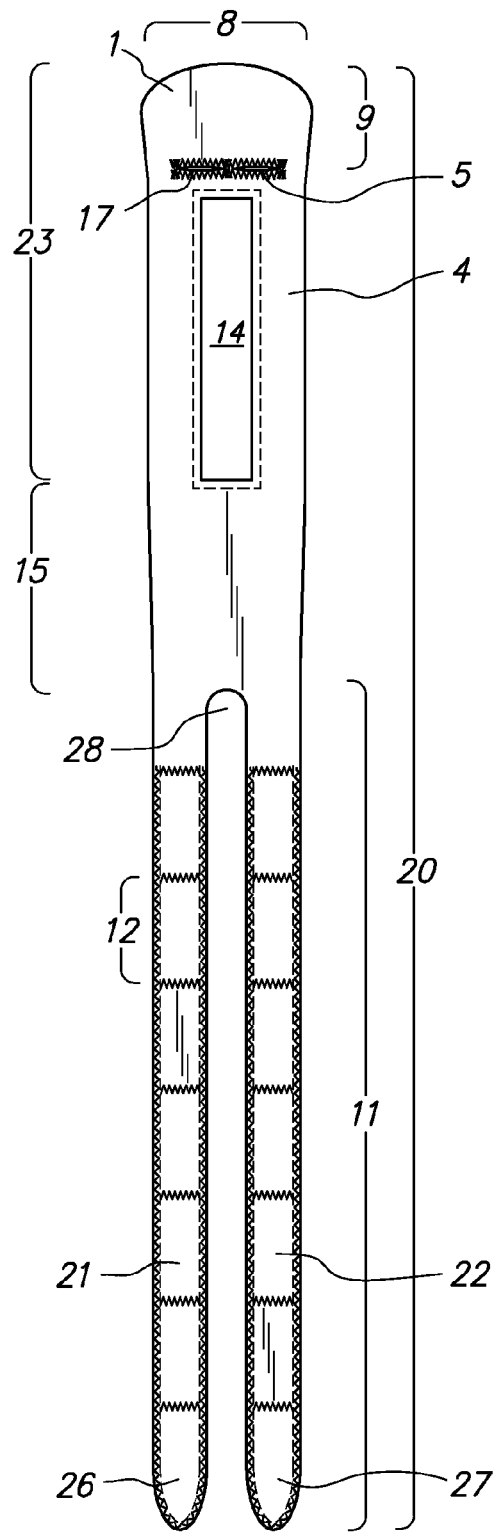
FIG. 6 shows a bottom plan view of a basic embodiment of the DRUJ Brace constructed with a single plastic sheet and equipped with fastening means comprising mating-halves reclosable fasteners.

FIG. 6 shows a top plan view of a basic embodiment of the DRUJ Brace constructed with a single plastic sheet and equipped with fastening means comprising cam-lock fasteners affixed to the top of the sheet. The sheet can be injection molded, and fastening means affixed during injection molding. Other means known in the art of attachment of cam-lock fasteners to plastic sheets can be used, e.g., riveting, sewing, adhesives, heat welding, and heat fusion.

The basic embodiments of the invention all have a single sheet (1), called the "primary sheet". The primary sheet material is typically a washable, inelastic, woven textile. The bottom of a textile primary sheet may be woven or processed to create a soft surface, e.g., woven pile, finishing by knapping or abrasion. Plastic primary sheets can be made from various types of flexible, inelastic plastic, e.g., extruded plastic, injection molded plastic. Various means known in the art of attachment of mating-halves reclosable fasteners to plastic sheets can be used, e.g., sewing, adhesives, heat welding, and heat fusion. The type of plastic is selected for its elastomeric, tactile, hypoallergenic, and durable properties.

A plastic primary sheet can be processed to have contoured edges along the margins (including the cutout) and a soft-feeling bottom surface. Injection molded sheets can also be made using "two shot injection" in which a first plastic resin is used to create a top, inelastic layer and a second plastic resin is used to create a bottom, soft-feeling layer. As shown in FIGS. 5, 6, 7, and 8, the fastening means can be embedded in a plastic primary sheet during injection molding.

Figure 7:
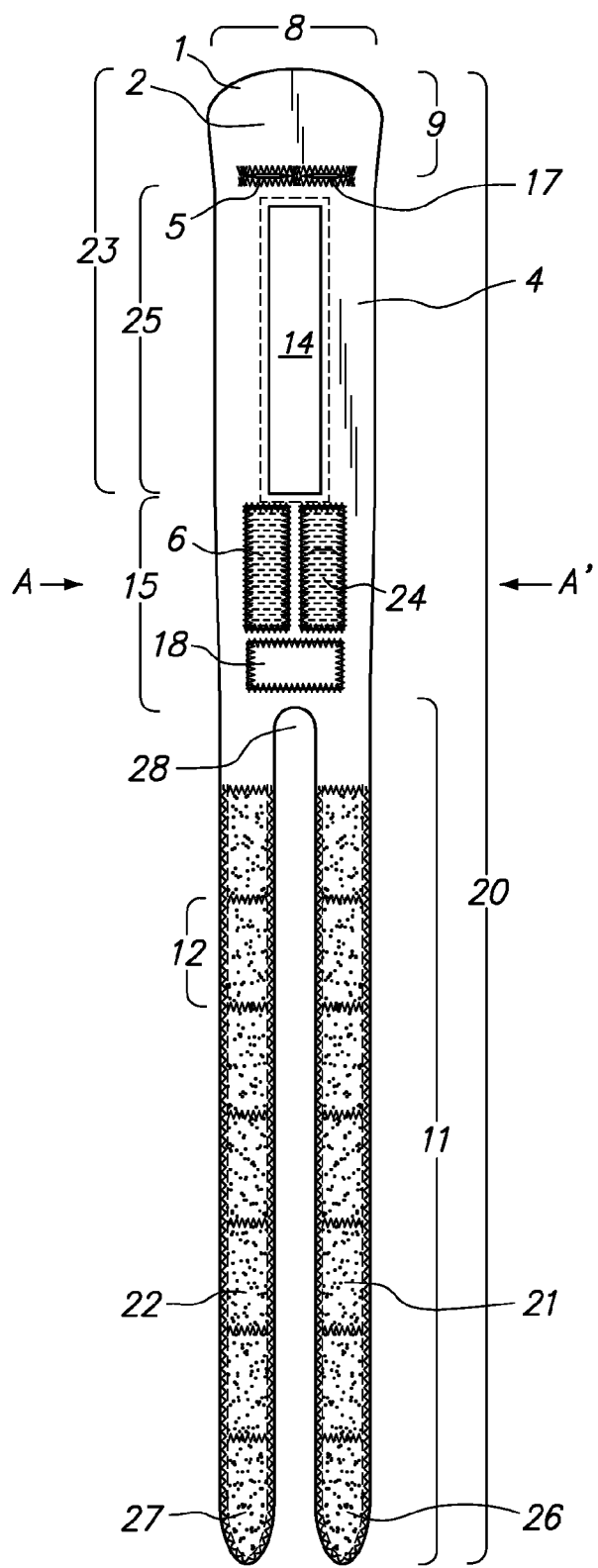
FIG. 7 shows a top plan view of a basic embodiment of the DRUJ Brace constructed with a two-shot, injection-molded plastic sheet and equipped with fastening means comprising mating-halves reclosable fasteners affixed to the top of the sheet during injection molding.

FIG. 7 shows a top plan view of a basic embodiment of the DRUJ Brace constructed with a two-shot, injection-molded plastic sheet and equipped with fastening means comprising mating-halves reclosable fasteners, such as hook and loop or mushroom head, affixed to the top of the sheet during injection molding. Other means known in the art of attachment of mating-halves reclosable fasteners to plastic sheets can be used, e.g., sewing, adhesives, heat welding, and heat fusion.

Figure 8:
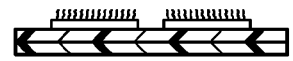
FIG. 8 shows a cross-section along axis A-A' of FIG. 7.

FIG. 8 shows a cross-section along axis A-A' of FIG. 7.

A preferred embodiment adds to the structure of the single-sheet embodiments described above a second flexible, inelastic sheet ("comfort sheet") affixed underneath the first sheet primary sheet, i.e., the comfort sheet is affixed to the primary sheet so that the surface in immediate contact with a patient's skin is the bottom of the comfort sheet. The comfort sheet typically covers not only the area of the primary sheet but also the area of the cutout (14). Embodiments that have a primary sheet and a comfort sheet are called "two-sheet embodiments". In all two sheet embodiments of the DRUJ Brace, when the DRUJ Brace is donned, the bottom of the comfort sheet is in immediate contact with the patient's skin, and the comfort sheet is selected in large part based on its tactile qualities.

Single sheet embodiments that use woven textile material typically have hemmed edges to minimize fraying of the fabric and irritation of the patient's skin. The comfort sheet material is typically a washable, somewhat elastic, woven textile. The margins of a textile comfort sheet typically are wrapped around the margin of the primary sheet and affixed in a hem.

A comfort sheet can be laminated to a primary sheet by adhesive or other laminating means known in the art. For instance, a plastic primary sheet can have a textile comfort sheet laminated underneath the primary sheet.

FIG. 9 shows a top plan view of a two-sheet, textile embodiment of the DRUJ Brace equipped with fastening means comprising sewn-on, mating-halves reclosable fasteners.

FIG. 10 shows a bottom plan view of a two-sheet, textile embodiment of the DRUJ Brace equipped with fastening means comprising sewn-on, mating-halves reclosable fasteners.

Figure 11:
FIG. 11 shows a cross-section view of FIG. 9, longitudinal axis A-A' (cutout area).

FIG. 11 shows a cross-section view of FIG. 9, longitudinal axis A-A' (cutout area).

Figure 12:
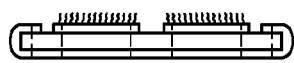
FIG. 12 shows a cross-section view of FIG. 9, longitudinal axis B-B' (reclosable fasteners area).

FIG. 12 shows a cross-section view of FIG. 9, longitudinal axis B-B' (reclosable fasteners area).

Figure 13:
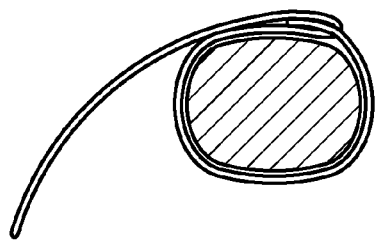
FIG. 13 shows a longitudinal cross-section view in the reclosable fasteners area of a donned DRUJ Brace of FIG. 9.

FIG. 13 shows a longitudinal cross-section view of a donned DRUJ Brace of FIG. 9 in the reclosable fasteners area. In this view the mating halves of a hook and loop fastener in the central section have engaged the opposite mating halves on the straps, thereby maintaining the straps in a tensioned state and thereby maintaining centripetal compression of the DRUJ area.

Length indications (12) can optionally be provided on the first and/or second straps. The junction of the first strap and second strip with the central section is at approximately the midpoint of the length of the DRUJ Brace. The slits in embodiments of the DRUJ Brace with textile primary sheets are preferably reinforced with stitching.

The materials used for the primary sheet and the comfort sheet are selected as a function of elasticity, thickness, flexibility, ease of handling during manufacturing, cost, breathability, ease of donning, doffing, and washing, and patient comfort. Sheet materials must not be so flexible that they deform easily in the longitudinal axis. Embodiments of the DRUJ Brace for the health care market would typically be two-sheet embodiments manufactured with higher quality textile materials. "Higher quality textile materials" means very minor deviations in elasticity, thickness, and flexibility over time and material lots, easier to handling during manufacturing, very breathable, easy to don and doff, stable after multiple washes, and comfortable to wear for long periods, e.g., continuously for six weeks.

Embodiments made of lower quality materials, such as injection molded plastics, would have a lower cost of manufacturing and a correspondingly lower price point. Lower quality materials would have greater deviations in elasticity, thickness, and flexibility over time and material lots, be harder to handle during manufacturing, have poor or nil breathability, be more difficult to don and doff, lose stability after multiple washes, and be less comfortable to wear for long periods. Embodiments made of lower quality materials could be acceptable, however, for preventive use in sports (tennis, golf, weightlifting, bowling) and manual labor where a range of price points is important. Fasteners add significant cost to the DRUJ Brace. Broadly speaking, the easier a fastener is to use, the higher the cost. For instance, button, snap, and clasp fasteners are difficult to fasten unilaterally, and are more difficult to affix to a primary sheet, but cost far less than mating-halves reclosable fasteners and cam-lock fasteners. Button, snap, clasp, D-ring, and C-ring metal and plastic fasteners can be used instead of mating-halves reclosable fasteners to achieve a lower price point.

The planar width of the straps can be dimensioned to create a small, medium and large sizes of DRUJ Brace; the approximate planar width of the straps of these sizes is approximately 12 to 15 cm, 15 to 18 cm., and 18 to 21 cm, respectively. Having a unilateral, "one size fits all", size has significant manufacturing, distribution, and stocking advantages. The length described here is to accommodate the range of average human wrist circumferences and is represented in the splint from the button holes to the split of the straps extending onward.

Neoprene and other types of polymer foams sewn with a zig-zag stitch can create a non-elastic sheet that is comfortable to wear. However, neoprene is much more expensive than available flexible, non-elastic, textiles, and is more difficult to handle in manufacturing. Despite its costs, zig-zag stitched neoprene can be used to make DRUJ Braces for certain product/markets, such as watersports.

Leather can be used as a primary sheet. Leather is durable and very stylish, but it is expensive, is often in short supply, has significant deviations in elasticity, thickness, and flexibility over time and material lots, is not very washable or breathable, and stains easily from perspiration. For high-style activities with short periods of use, such as golf, leather embodiments might have a good market.

The planer length of the primary sheet can be increased to approximately 9 cm to provide increased support proximally from the ulnar styloid. The planar strap length (longitudinal axis) of the distal strap and slit length for the distal strap could be increased up to approximately 2 cm and 2.1 cm, respectively, and the planar strap length (longitudinal axis) of the proximal strap and slit length for the proximal strap could be increased up to approximately 6 cm and 6.1 cm, respectively. The support of the wrist would be wider and less comfortable but the mechanism of the squeeze would not be compromised. This embodiment could be donned in two ways on the dextral and sinistral DRUJ areas.

Although DRUJ Braces can be custom-made for a specific DRUJ area circumference, i.e., made with one position fasteners, such embodiments deprive a patient of the ability to adjust the compressive force of the DRUJ Brace to reflect a given task or activity. For instance, more compressive force would be needed when bowling than when sleeping.

The straps of a DRUJ Brace allow it to accommodate a wide range of anthropometric variation in DRUJ area without the need of multiple sizes of the DRUJ Brace. Typically, only pediatric and adult sizes of the DRUJ Brace are kept in inventory.

FIG. 14 shows a perspective view of a first way of wearing a DRUJ Brace. As shown in FIG. 14, to use a DRUJ Brace with hook/loop fastening means, the patient typically guides the first strap through the corresponding first slit in the end section, guides the second strap through the corresponding second slit in the end section, thereby configuring the DRUJ Brace as a cylinder with two protruding straps, then slips the DRUJ Brace over the patient's hand and wrist until the dorsal section of the DRUJ Brace overlies the dorsal surface of the DRUJ area with one marginal area skirting the distal side of the ulnar styloid ("distal strap") and the second marginal area skirting the proximal side of the ulnar styloid ("proximal strap"). The patient places the volar surface of the DRUJ Brace against a flat surface to stabilize position of straps around the ulnar styloid, pulls both straps medially (i.e., back toward the dorsal section) to tighten the DRUJ Brace around the DRUJ area, then firmly presses the bottom of each strap against the corresponding mating portion of the fastening means on the dorsal section of the DRUJ Brace. The distal strap can be independently tensioned to apply an appropriate compressive force on the distal portion of the DRUJ. The proximal strap can be independently tensioned to apply an appropriate compressive force on the proximal portion of the DRUJ. The compressive force of each strap can be easily, rapidly, and independently adjusted by pulling a given strap off the fastening means on the dorsal section, retensioning the strap, and firmly pressing the bottom of the strap against the corresponding mating portion of the fastening means on the dorsal section of the DRUJ Brace.

FIG. 15 shows a perspective view of a second way of wearing a DRUJ Brace in which the straps straddle the ulnar styloid.

A patient can apply and adjust a DRUJ Brace unilaterally. The DRUJ Brace conforms closely and comfortably to the contours of the DRUJ area. The strap tension is typically increased for load-bearing tasks and decreased for non-load-bearing tasks. Load-bearing tasks include both work tasks and sports activities, such as tennis, golf, bowling, gardening, and weightlifting. The DRUJ Brace provides adjustable support of the DRUJ and TFCC, decreases DRUJ and TFCC arising from function, work and sports, increases grip strength, provides support through supination and pronation of the wrist, increases weight bearing of the wrist, decreases pain with grip, and decreases pain with weight bearing. Prophylactic use helps to prevent DRUJ and TFCC injury, and extensor carpi ulnaris subluxation. Post-injury and post-surgery use helps to heal the DRUJ and TFCC. Embodiments of the DRUJ Brace also be made using consumer quality materials for retail sales, and higher quality materials for clinical and institutional uses. The DRUJ Brace, when made of the preferred materials and washed regularly, avoids skin breakdown or irritation of the skin, even when worn for several weeks. The DRUJ Brace is low profile and does not interfere with wrist motion. The DRUJ Brace can be worn wet and will adequately dry without removal.

When using a DRUJ Brace, the lack of immobilization of wrist flexion and extension allows improved function with less risk. No inclusion of the thumb, elbow, and fingers is a key design element and benefit of the DRUJ Brace, and avoids risk of stiffness associated with joint immobility. There is no risk of tendonitis.

Diagnoses for which the DRUJ Brace is indicated include TFCC sprains and tears, distal radius and/or ulnar fractures, DRUJ injuries, extensor carpi ulnaris subluxation, ulnar styloidectomy, DeQuervyn's tenosynovitis, scaphoid fractures, Rheumatoid Arthritis, scaphoid lunate dissociation. Prophylactic use of the DRUJ Brace is recommended for prevention of injury for, inter alia, tennis players, golfers, bowlers, and weightlifters, yoga practitioners, and carpenters who have a high risk of injury to their wrists.

The fasteners discussed herein are all been based on the hook and loop fastener type of technology. In addition to this technology, other fasteners might include snaps, pins, or other hook and claw arrangements. Other fastening means add cost and complexity, however, and may irritate the skin, DRUJ area, or wrist.

While the invention has been described with reference to specific embodiments thereof, it will be understood that numerous variations, modifications and additional embodiments are possible, and all such variations, modifications, and embodiments are to be regarded as being within the spirit and scope of the invention.

I claim:

1. A brace arranged for securement over a wearer's distal radioulnar joint, said brace comprising:
   a. a first strap having a width and arranged for adjustably compressing the proximal portion of the distal radioulnar joint;
   b. a second strap having a width and arranged for adjustably compressing the distal portion of the distal radioulnar joint;
   c. a fastener associated with each strap for maintaining compression of the radioulnar joint;
   d. said brace formed of a flexible inelastic primary sheet and including a cutout section including an oblong cutout of said sheet to form a first marginal area and a second marginal area, each marginal area being approximately the same width as the first and second straps, said oblong cutout arranged to be disposed over the ulnar styloid when the brace is worn; and,
   e. wherein when worn, said brace does not compress the ulnar styloid and wherein no portion of said brace extends distally beyond the wearer's distal radioulnar joint onto the wearer's hand so as to enable full wrist motion including flexion and extension.

2. The brace of claim 1, additionally comprising a central section adjacent a first end of said cutout section, said central section comprising a lateral side, said first and second straps being integral with said central section and extending from said lateral side.

3. The brace of claim 2, additionally comprising a rounded grip section adjacent a second end of said cutout section, said rounded grip including a first and second slits aligned with said first and second straps and
   a first fastener in said central section aligned with said first strap, and a second fastener in said central section aligned with said second strap, wherein a portion of each respective fastener may optionally be disposed on each of said two straps.

4. The brace of claim 3, wherein each said fastener comprises mating-halves reclosable fasteners selected from the group consisting of hook and loop fasteners and a-mushroom head fasteners.

5. The brace of claim 3, wherein each fastener comprises a cam-lock fastener.

6. The brace of claim 3, wherein the brace further comprises a comfort sheet.

7. The brace of claim 6, wherein a comfort sheet is affixed to the bottom of said primary sheet.

8. The brace of claim 3 manufactured using materials selected from the group consisting of textile, leather, polymer foam, and plastic.

9. The brace of claim 3 manufactured using injection molded plastic.

10. The brace of claim 1, wherein compression provided by said first strap is independent of compression provided by said second strap.

* * * * *